United States Patent [19]

Wilson et al.

[11] 4,360,887
[45] Nov. 23, 1982

[54] SKIN CATEGORIZING APPARATUS

[75] Inventors: Raymond L. Wilson, Liverpool, England; James A. Dingwall, Edinburgh, Scotland

[73] Assignee: Edward Wilson & Son Limited, England

[21] Appl. No.: 173,922

[22] Filed: Jul. 31, 1980

[30] Foreign Application Priority Data

Aug. 4, 1979 [GB] United Kingdom ............... 7927246

[51] Int. Cl.³ .......................................... G06F 15/46
[52] U.S. Cl. .................................. 364/552; 364/478; 358/107; 356/357
[58] Field of Search ............... 364/469, 475, 478, 552, 364/564, 550, 560, 551; 358/107; 69/1, 21; 356/357; 198/340; 250/571

[56] References Cited

U.S. PATENT DOCUMENTS

| | | | |
|---|---|---|---|
| 2,184,156 | 12/1939 | Bowles | 358/107 X |
| 2,184,159 | 12/1939 | Stockbarger et al. | 358/107 X |
| 2,447,024 | 4/1948 | Metcalf | 358/107 X |
| 3,754,123 | 8/1973 | Keller | 364/560 |
| 3,940,998 | 3/1976 | Sourby et al. | 364/475 X |
| 4,132,314 | 1/1979 | von Beckmann et al. | 364/478 X |
| 4,195,346 | 3/1980 | Schroder | 364/478 X |
| 4,239,434 | 12/1980 | Gannon | 364/478 X |

Primary Examiner—Edward J. Wise
Attorney, Agent, or Firm—William A. Drucker

[57] ABSTRACT

Skin categorizing apparatus comprises a conveyor on which skins are categorized by automatic area scanning and thickness measuring means generating data for transmission to a remote location for control and data processing equipment. Displays at the conveyor location are driven by the control equipment to show data first transmitted thereto. The area and thickness means is capable of dealing with a single skin or two sides of split skins simultaneously. Thus two sets of displays are shown one at each side of the conveyor. Data entry means serves for a skin quality input and data generation with an associated display. The control equipment includes a supervisor's display unit and two printers one for logging work progress and the other for printing out batch labels or advices when a batch is complete for a particular order.

12 Claims, 5 Drawing Figures

SKIN CATEGORIZING APPARATUS

The invention relates to apparatus for use in categorising hides, skins, pelts and the like (all hereinafter referred to as "skins").

We have previously made proposals for that purpose and in relation to thickness, area and quality of skins, especially in relation to the tanning industry where particular requirements arise for categorising at an intermediate stage of tanning, e.g. what is referred to as the "wet-blue" stage. Our previous proposals have included automatic area and thickness measurement, but certain difficulties have been encountered in controlling conditions within tanneries so that display and batch product control apparatus will operate reliably and give all information required by a supervisor in a convenient manner.

Thus, it is customary to categorise input lots or batches of skins both on an individual category basis and on all-in area basis. Also, it is desirable to satisfy orders, or output skins, on a batch basis with an automatic indication of when any particular order is satisfied.

We now believe that these and other desirable features are best achieved by way of a system that provides displays and data entry locally to a categorising table or conveyor, but also provides for collecting displaying, processing and transmitting data automatically and/or selectively under supervisor control at, and transmission circuit driving from, a location remote from skin processing and categorising, which location is more readily provided with suitable conditions for electronic apparatus and affords better supervisor control and access to information.

We have been materially aided by such a system in providing additional facilities including a capability for a categorising table or conveyor to process simultaneously two separate sides, or halves of complete skins. This facility is readily afforded by area measuring means that spans the width of the conveyor but capable of providing separate outputs concerning two side portions thereof, normally each to a different side of a centre line. Also, separate thickness gauging devices may be associated with those side portions, respectively, for example spring-loaded wheels or rollers whose deflection is measured. Quality is, of course, still best judged by skilled operators and information keyed by them into a system such as that above-mentioned.

We therefore prefer to provide two sets of categorising and data generation equipment, one to each side of a categorising conveyor.

An advantage arises in that whole skins can be categorised simply by scanning area information concerning the two side portions, taking either of the thickness outputs alone or averaging both, and, normally, allowing one quality facility to prevail. Obviously, however, each side of the same whole skin may be categorised individually if desired, so long as it straddles the side portion division of the area sensor.

We also prefer to provide a skin splitting device, such as a retractable blade, either immediately before or after the categorising conveyor.

Reverting particularly to our proposed remote supervision system, in preferred embodiments at least one set of multiple displays is provided at the categorising conveyor location, one for sensed area, one for sensed thickness, one for quality, all conveniently in a single console alongside the conveyor and separately linked for data reception from the remote data processing unit, and another located at the off-loading position for the conveyor and linked to the remote data processing unit for reception and display of area, thickness and quality grades for the last skin. Such displayed data will have been received from the conveyor location before transmission back to the displays. The or each said single console preferably incorporates a keyboard for quality input, say with one key for quality cancellation in order to correct a wrong quality input prior to data finalisation at the processing unit. The same or a further console alongside the conveyor preferably has a thickness input display and keyboard as a back-up for normal entry of thickness data should a thickness transducer or measuring-system fail.

Obviously, to allow for double-sided operation there will be separate sets of display and key-board console equipment at each side of the conveyor.

Normally, the supervisor location will have a visual display unit and control console or terminal coupled to the data processing unit. Preferably, the latter is also coupled to drive two printers, one for logging work progress and the other for printing batch labels or advices. Thus, concerning input work, logging will indicate which lot is concerned and will print out at least the number of skins and area information, although it will obviously be possible to print out detailed quality and thickness information too, and/or to classify according to quality categories based thereon. The logging printer thus keeps records of work throughput and can be printed out each work day or shift as desired. The batch labels or advices will normally concern output orders with an indicator for when any particular category has enough skins to satisfy a particular order, at which stage an alarm can be sounded automatically for resetting at a categoriser conveyor input console. The second printer will print out a label or advice accordingly, and corresponding information may be logged or available for print out on the first printer.

Certain aspects of preferred multiplexing and electro optical isolation couplings are also considered to be of great benefit in relation to minimising equipment connections at the conveyor location and maximising system integrity and reliability, as will become apparent herein.

One embodiment of the invention will now be described in more detail with reference to the accompanying drawings, in which.

Figure 1:
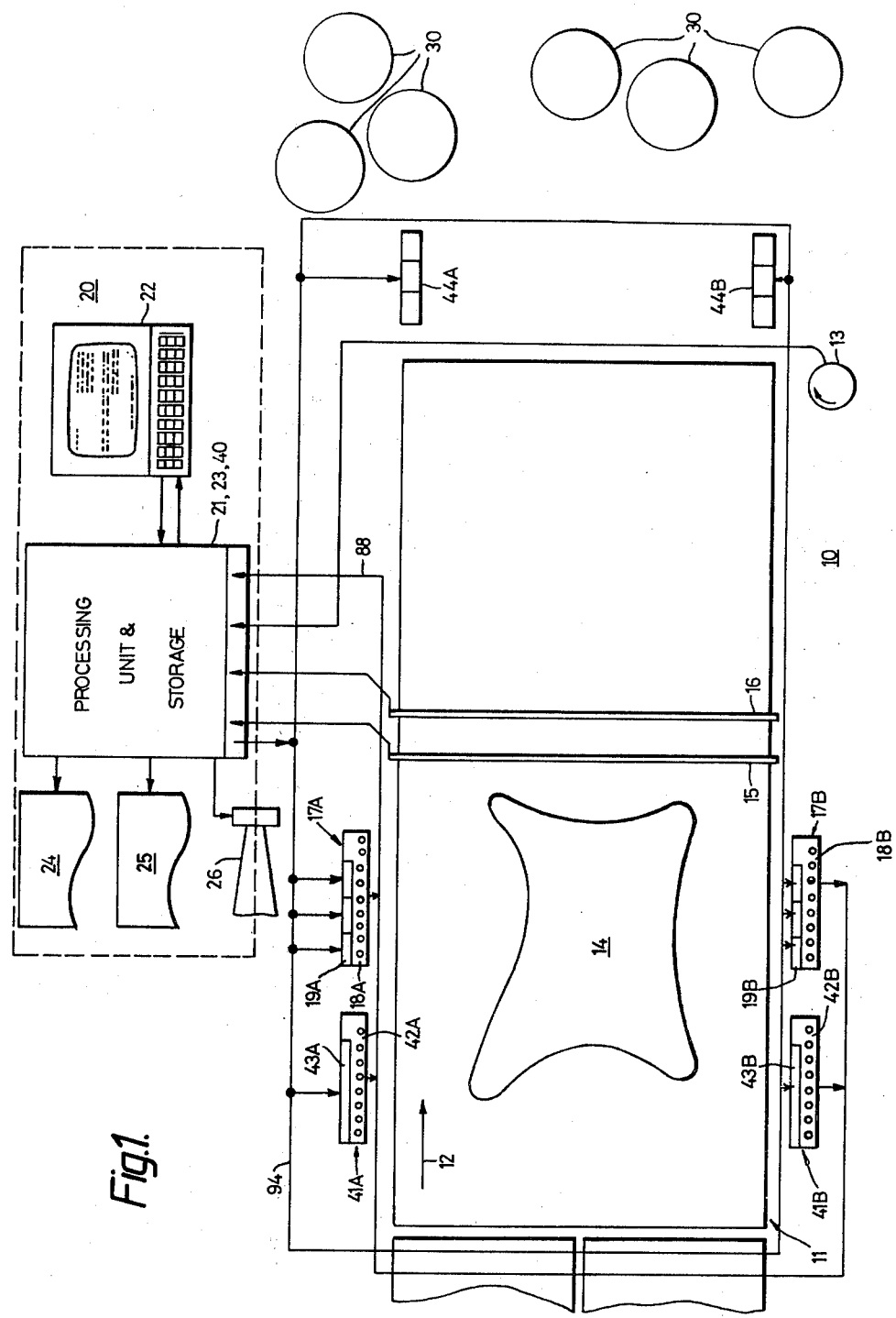
FIG. 1 is a diagram showing a typical installed system.

In the drawings, a categorising location 10 has a conveyor 11 driven in the direction of arrow 12 at a suitable speed sensed by a drive motor shaft encoder 13 or other speed sensing system or transducer preferably affording a digital output. One whole skin 14 is shown advancing along the conveyor 11 towards two measuring stations 15 and 16, the former for thickness and the latter for area. The thickness measuring transducers 15' (FIG. 2) comprise rollers one to each side of the conveyor, whose deflection is measured electrically, usually as an analogue signal supplied to an analogue-to-digital converter 46. Any other convenient form of thickness measuring system or transducer may be used. The area measuring station comprises a bridge carrying spaced photocells, for example sixty in number for a three meter-wide conveyor 11, that receive light reflected from the skins when a skin is under the bridge. Then, of course the conveyor itself would be relatively less reflective. The alternative arrangement is, of course, feasible with the conveyor and skins relatively more and less reflective, respectively, and the photocells off when a skin is under the bridge. Luminescent tube-type light sources shielded from directly illuminating the photocell are suitable.

The conveyor 11 also has associated therewith two sets of data input and/or display equipment, one to each side thereof. Thus, in consoles 17A and 17B are keyboards 18A and 18B and displays 19A and 19B. These keyboards have any desired number of keys, buttons or touch sensitive pads for input of different quality assessments of the skins in turn, and the displays are in two parts for the entered quality assessment as a decimal number (one digit) and for the area of the skin (3 digits), but could if desired also have a third part for the thickness of the skin (one digit).

Consoles 41A and 41B house further keyboards 42A and 42B and displays 43A and 43B. These keyboards are for thickness entry if the automatic thickness sensing fails or if it is preferred to measure and grade in some other way, and actually provides three digit accuracy on the displays correspond.

Additional displays 44A and 44B are shown at the off-loading end of the conveyor 11 and these are basically of three decimal digit type to show area, thickness and quality bands so as to identify the correct pile or pallet 30.

Clearly, the speed of the conveyor has to be taken into account for an area calculation. This is done at a remote supervisor's location 20 which can be environmentally distinct from the categorising location and houses a data processing unit 21, conveniently of silicon chip microcomputer technology, and a visual display unit and keyboard terminal 22. The supervisor is able to call up for display any data held by the data processing unit and its store 23 for processing as desired, as well as entering data and instructions for desired action and operation of the system. The supervisor's location also includes two separately operable printers 24 and 25. The first (24) is a standard computer-type line printer and is controlled by the processing unit to produce two types of print out. One concerns the sorting of a purchase lot of skins and lists, for each skin category, the lot number, the number of skins and the total area of those skins. It may also be convenient to list the total number of skins in the lot as that will usually be known ab initio. The other print-out is a time period print-out that makes a similar listing but only of skins processed in a particular time, such as a working day or shift, with an indication of whether any particular lot is active or finished. Both types of print-outs can be made available on demand, or the same information displayed on the supervisor's display unit, each with an indication whether or not the lot concerned is finished.

The other printer 25 is, in this embodiment, a smaller electrostatic printer for producing output batch reports again under control of the processing unit. The supervisor will enter order details by number of skins and/or total skin area and desired category or categories, and will be able to monitor progress of each order on the display. As soon as any particular category for an order is completed, that will be indicated and the second printer 25 will produce a report specifying the order, the category, the number of skins and their total area. We also prefer that report to break-down the number and area of skins according to purchase-lot origin. That report can simply be torn off the printer for attachment to the relevant category skin bundle or pallet.

The processing unit is also associated with one or more alarms, such as an audible device 26 and/or a light, so that both the supervisor and the conveyor personnel will be made aware that a category bundle or batch is complete and ready for labelling. Various batch piles or, more usually, pallets are shown at 30.

It will be appreciated that the processing unit receives data directly from the thickness sensors, the area bridge, the conveyor speed transducer, and the operator-entered quality indicator and transmitter, and also transmits data to the various displays and alarm(s) adjacent to the conveyor, via interfacing arrangements 31 to 36 at the supervisor location. It will be noted that most of these are coupled by way of electro-optical couplers 40 so that electrical noise and accidental short circuiting, which are likely in the adverse conditions common to a tannery, cannot affect the equipment at the supervisor location. In addition to avoiding mechanical or soldered connections, such an arrangement also readily permits compensation to be made for different lengths of cable runs by the provision of buffering amplifiers, perhaps individually adjustable, for feeding each of the electro-optical isolating arrangements. Also, of course, this mode of operation ensures that the processing unit has the correct data from the keyboard. In this way, a very high degree of system integrity and reliability is obtained that would otherwise be unattainable in the often difficult dirt/humidity conditions of a skin processing plant.

All of the displays at the conveyor location are of a latched type so that, once loaded by the processing unit, they will continue to display until reloaded, and thus will always represent the current situation. This latching also, of course, facilitates the displays being multiplexed to the processing unit. The keyboards will also be multiplexed and each may include one additional key that confirms entered data once the display has been checked. This retransmission is preferred to locally generated display of entered data for the reasons mentioned above for reliability and equipment integrity. However, local generation is feasible with any said additional key then serving to enable transmission rather than confirm entry into the processing unit.

Figure 2:
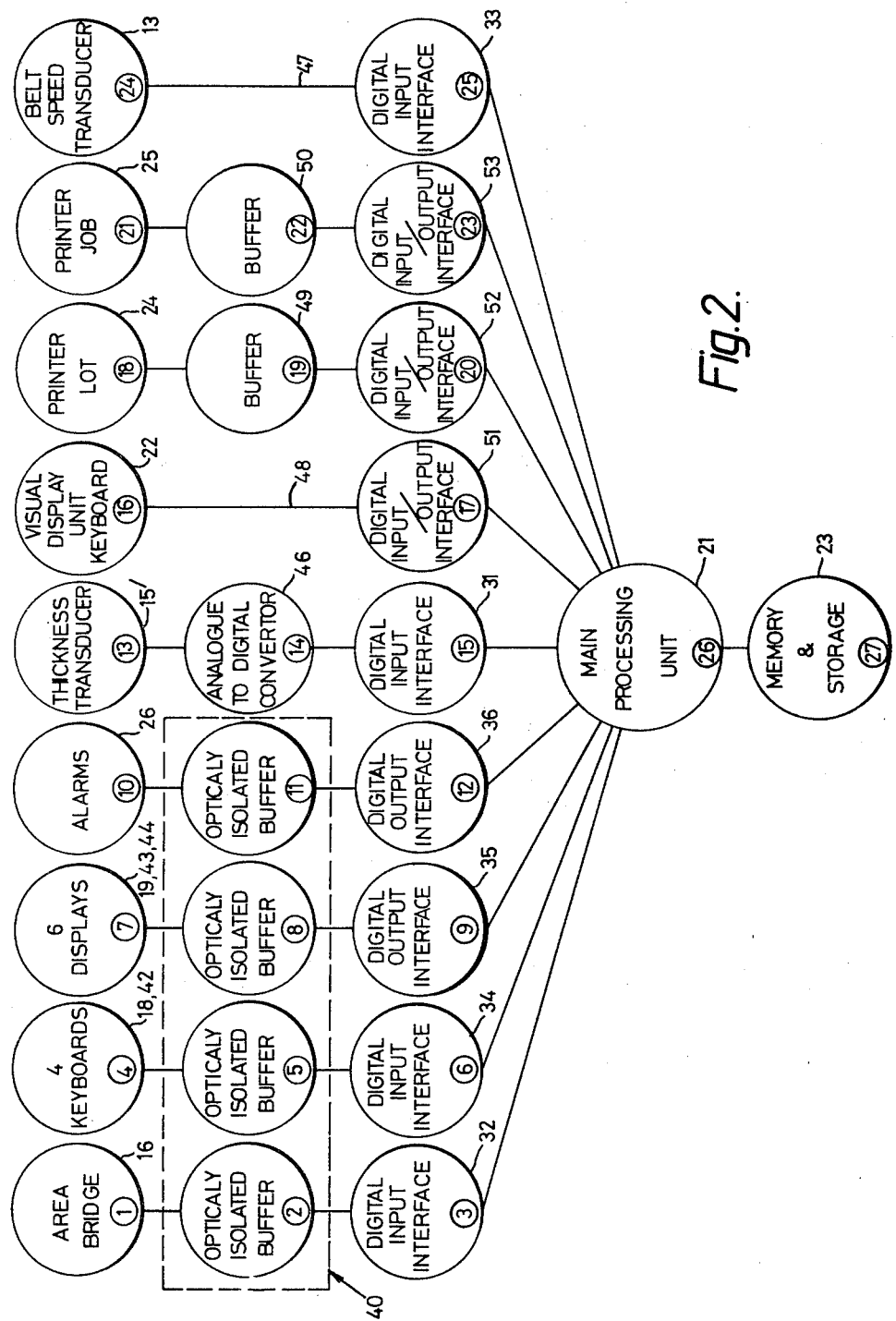
FIG. 2 is a block diagram of a typical system.

FIG. 2 shows the analogue-to-digital converter 46 for the thickness transducer and that will be at the supervisor location. No electro-optic isolation is shown for that or for the conveyor speed transducer, typically an optical shaft encoder, as we have found that a screened cable 47 is generally adequate for the latter. However, electro-optic isolation may be used and could be preferred in some environmental conditions.

Direct parallel communication 48 is shown to the supervisor's terminal and buffered communication 49, 50 to the printers 24, 25, from interfaces 51, 52 and 53.

Figure 3:
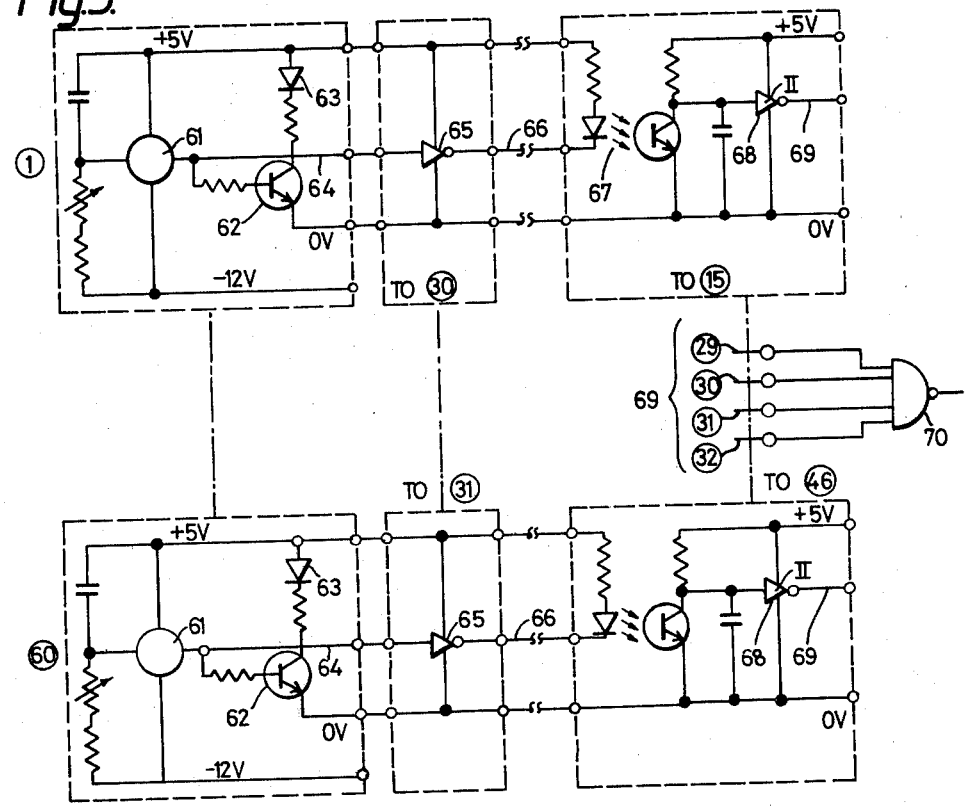
FIG. 3 shows area sensing details.

One particular arrangement of area bridge circuitry is indicated in FIG. 3. Briefly, each photocell 61 is associated on its own printed circuit board with a transistor 62 and a light emitting diode 63 so as to produce an output signal on line 64 when the photocell is illuminated and the light emitting diode is lit. The photocell 61 and light emitting diode 63 are conveniently on opposite sides of the card so that the former will be exposed to light reflected from the skin and the latter will indicate that condition. Output 64 is applied to a buffering amplifier 65 to apply a desired amplitude of signal to transmission line 66 extending to an electro-optic isolation circuit 67 associated with a Schmit trigger 68 and providing an output 69 at the supervisor's location. It is convenient for the buffer amplifiers 65 to be mounted on two printed circuit boards, one for each half of the area bridge, and the electro-optic-isolators 66 will normally be mounted on four boards each corresponding to one quarter of the width of the conveyor. If desired, signal variation may be obtained using the variable resistor to the photocell, and the buffers too may be at the supervisor location.

One way to ensure automatic detection of whether whole skins or sides only are present is to sense the state of one or more of medial ones of the photocells, say by a logic gate 70 connected to outputs of the middle four of the electro-optic isolator circuits, perhaps preferably a NAND gate to indicate that at least one of those photocells is not energised. If that is the case, outputs from both halves of the area bridge will be treated separately using information via the equipment at different sides of the conveyor, otherwise the area information would be summed for both halves and only one for an average of the thickness transducer outputs and quality inputs taken account of. Obviously, however, conveyor operator or supervisor mode switching or optical instruction could be utilised to set up for simultaneous sides or whole skin types of operation.

Figure 4:
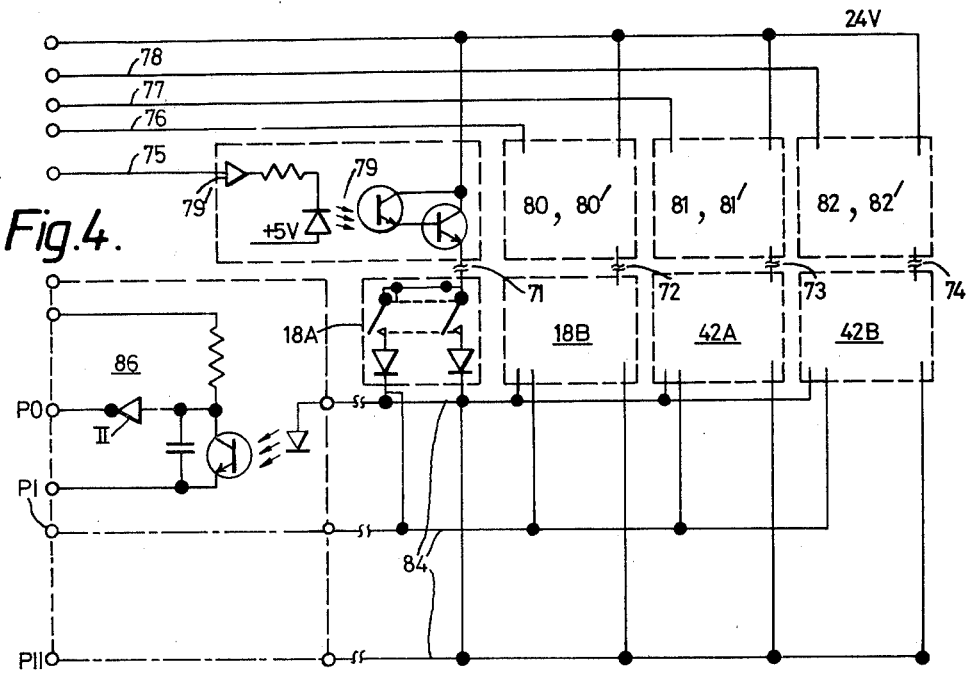
FIG. 4 shows keyboard multiplexing.

The preferred way in which isolation and multiplexing is achieved for the keyboards is shown in FIG. 4 where supply lines 71 to 74 for the keyboards, respectively, are energised in time sequence from scanned lives 75 to 78 via electro-optic isolators 79 to 82, each with buffers 79' to 82'.

The individual key output lines of the keyboards are connected in to a common set of lines 84 equal in number to the number of keys for each keyboard and these are returned to the supervisor location and coupled via corresponding electro-optic isolator channels 86. The double isolation of supply enable and return lines is a substantial advantage as the keyboards are then energised only when intergrated at a scan rate very much faster than operator depression time but also slower than any key-bounce time. Obviously, the use of touch conductivity pads would render the latter consideration unnecessary. At least eight and preferably ten, quality or thickness grade possibilities are provided for by individual keys with a further key acting to clear data. If desired, a yet further key can serve to confirm to the processing unit that the information displayed matches that sent. In general, however, the information is conveniently taken as being correct at the time that the area bridge begins to transmit skin signals. FIG. 2 shows the keyboards connected to a common bus 88.

Figure 5:
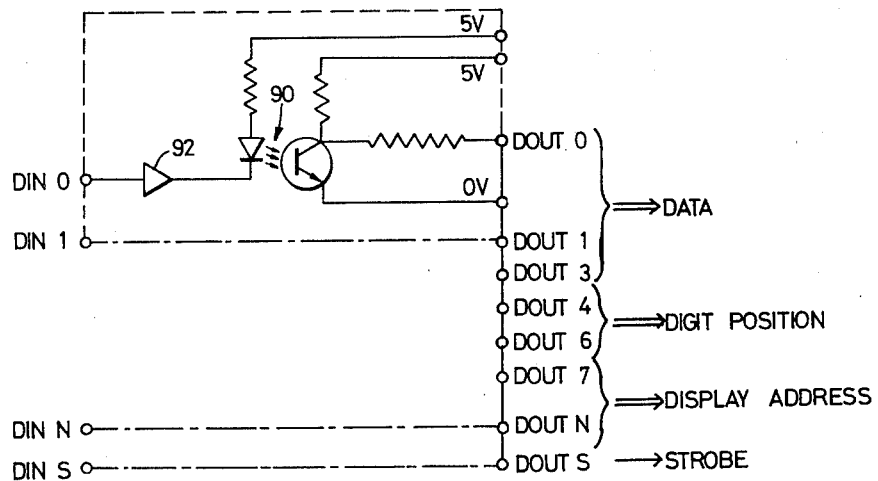
FIG. 5 shows display coupling.

FIG. 5 shows the preferred way of multiplexing transmission to the displays, each of which is individually addressable and thus enabled according to output DOUT 7 to DOUT N. Further addressing is provided for an output DOUT 4 to DOUT 6 in order to identify the digit position required, and binary data is provided on lines DOUT 0 to DOUT 3 for energisation of binary-to-decimal display decoder at the relevant digit position. A strobe output DOUT 5 is also provided for control of updating the displays only when required, i.e. for each new skin. Each of the DOUT terminals is connected by an electro-optical isolator 90 and buffer drive 92 channel to input terminals D/N from the processing unit. FIG. 2 shows all of the displays connected to a loop bus 94.

FIG. 1 shows a skin cutting station at the loading end of conveyor 11, with a slot to coobe used for converting full skins into sides. It is also a preferred feature of this invention that an automatically operable shier be disposed at the off loading end of the conveyor 11, whether or not a shier is provided at the input end. The output shier can then be automatically operated by the data processing unit if the quality of a whole skin is below a level indicating a good whole hide, say 6 or 7 on an 8-grade scale.

Some of the functions described herein, for example side or whole skin setting, are attainable by computer programming. However, that feature as a facility is extremely useful and does require two sets of input and display equipment other features hereof, including dual printers and the basic system integrity offered by transmission of data out of the conveyor location and then transmitting back to displays at the conveyor location, especially with isolation whether electro-optical or other non-direct-wired type, and the buffering of signals to match connection lines, are specifically related to and improve skin grading operations.

Other specific features not yet mentioned but of potential advantage include the use of the area part of the displays 19A and 19B for alternatively showing classification as per displays 44A and 44B, at least at the stage where the area data has been transmitted and displayed, i.e. at off-loading. This can be a useful back-up to the displays 44A and 44B.

Also, the use of an electrostatic type of label or batch report printer 25 has the advantage that paper therefor may be water- and fade-resistant, which is of obvious advantage for skin batches that maybe wet.

We have indicated that sixty photocells are used in the area bridge and that electro-optic isolator boards are preferably four in number. Conventional electronic circuitry modularity, especially for digital applications tends to be in binary powers so that four otherwise spare channels may be used for indication of any light failure in the associated group of channels, especially where each area photocell has its own illuminating device, which could, in fact be a or said light emitting diode that is permanently energised.

Finally, we prefer also to include in at least output of the printer 25 an indication of whole skins or sides only, even indicating whether the latter are left or right hand sides. Conveniently, those left and right hand indications are correlated simply with left and right hand siHowever a system that automatically assumes that to be the case is advantageous.

We claim:

1. Skin categorizing apparatus comprising, at a first location, a bed support on which skins laid out flat are to be categorized, scanning means for generating data signals concerning area of a skin, means for displaying categorizing data concerning area, thickness and quality, and data entry means at least for skin quality; means for transmitting data between the first location and a second location remote from the first location, the means for transmitting including electrical conductor connection of the locations and electronic driver means at said second location to activate and drive said electrical conductor connection for all said data transmission; and further at said second location, means for controlling transmission of data signals from the first location, and for collecting, displaying and processing that data to individual skin category form, in either of automatic or selective modes under supervisor control.

2. Apparatus according to claim 1, comprising means operable automatically with said scanning means during movement relative to the support for generating data signals relating to thickness of a skin, area and thickness data signals being transmitted directly to the second location for retransmission therefrom to the first location for operation of the display means thereat.

3. Apparatus according to claim 2, wherein displays for area, thickness and quality data at the first location are parts of a multiple display unit alongside the conveyor, but with separate links for data reception from means at the remote second location, and wherein another display is located at a conveyor off-loading position of the first location and also linked to the means at the remote second location for reception and display of area, thickness and quality data for the last skin categorised.

4. Apparatus according to claim 3, wherein said unit further includes a keyboard for input of quality data, that keyboard having a device for cancelling quality data so that it can be corrected prior to data finalization by the means of the remote second location.

5. Apparatus according to claim 3 or claim 4, further comprising, alongside said support, data entry and display means for thickness data as an alternative to automatic generation thereof.

6. Apparatus according to claim 1, wherein, at said second location, the means for transmitting includes interfacing equipment (31–36) to said means for controlling, which interfacing equipment includes multiplexing means for cyclical data collection and display data transmission.

7. Apparatus according to claim 6, wherein said interfacing equipment includes electro-optic isolating means.

8. Apparatus according to claim 7, wherein the data entry means includes two or more keyboard units energised in sequence via electro-optic isolators and sharing data entry lines also coupled via electro-optic isolators.

9. Apparatus according to claim 7 or claim 8, wherein display data transmission to the first location is also via electro-optic isolation means for data and display address lines.

10. Apparatus according to claim 1, wherein at least area scanning and data generating means at the first location is operative selectively for whole skins or simultaneously for separate sides of split skins, and further comprising at the first location separate sets of display and data entry means one to each side of the support for such said separate sides of split skins respectively.

11. Apparatus according to claim 1, wherein the means for controlling comprises a visual display unit and control console coupled to a data processing unit, and two printers, one controlled to log work progress and the other controlled to print batch labels or advices.

12. Apparatus according to claim 11, further comprising an alarm or scanning indicator operative when a said output order batch is complete.

* * * * *